US009000021B2

(12) United States Patent
Sundaram et al.

(10) Patent No.: US 9,000,021 B2
(45) Date of Patent: *Apr. 7, 2015

(54) METHOD OF TREATING BENDAMUSTINE-RESPONSIVE CONDITIONS IN PATIENTS REQUIRING REDUCED VOLUMES FOR ADMINISTRATION

(71) Applicant: Eagle Pharmaceuticals, Inc., Woodcliff Lake, NJ (US)

(72) Inventors: Srikanth Sundaram, Somerset, NJ (US); Scott L. Tarriff, Mahwah, NJ (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,267

(22) Filed: Mar. 15, 2013

(65) Prior Publication Data

US 2013/0253026 A1 Sep. 26, 2013

Related U.S. Application Data

(60) Provisional application No. 61/613,173, filed on Mar. 20, 2012, provisional application No. 61/669,889, filed on Jul. 10, 2012, provisional application No. 61/678,715, filed on Aug. 2, 2012.

(51) Int. Cl.
A61K 31/4184 (2006.01)

(52) U.S. Cl.
CPC .................................. *A61K 31/4184* (2013.01)

(58) Field of Classification Search
CPC ............................ A61K 31/41; A61K 31/4184
See application file for complete search history.

(56) References Cited

U.S. PATENT DOCUMENTS

| 4,711,906 | A | 12/1987 | von Stetten et al. |
| 7,772,274 | B1 | 8/2010 | Palepu |
| 8,076,366 | B2 | 12/2011 | Courvoisier et al. |
| 8,344,006 | B2 | 1/2013 | Drager et al. |
| 8,389,558 | B2 | 3/2013 | Alakhov et al. |
| 2004/0043069 | A1 | 3/2004 | Vanderbist et al. |
| 2005/0042285 | A1 | 2/2005 | Ukai et al. |
| 2006/0159713 | A1 | 7/2006 | Brittain et al. |
| 2008/0118544 | A1 | 5/2008 | Wang |
| 2009/0209606 | A1 | 8/2009 | Bendall et al. |
| 2009/0264488 | A1 | 10/2009 | Cooper et al. |
| 2010/0092474 | A1 | 4/2010 | Gallagher |
| 2010/0145266 | A1 | 6/2010 | Orlowski |
| 2010/0216858 | A1 | 8/2010 | Popek et al. |
| 2010/0273730 | A1 | 10/2010 | Hsu et al. |
| 2011/0015244 | A1 | 1/2011 | Alkhov et al. |
| 2011/0184036 | A1 | 7/2011 | Palepu et al. |
| 2011/0190363 | A1 | 8/2011 | Drager et al. |
| 2012/0059000 | A1 | 3/2012 | Ren et al. |
| 2012/0071532 | A1 | 3/2012 | Cooper et al. |
| 2012/0157505 | A1 | 6/2012 | La Bell et al. |
| 2013/0041003 | A1 | 2/2013 | Brittain et al. |
| 2013/0041004 | A1 | 2/2013 | Drager et al. |
| 2013/0210878 | A1* | 8/2013 | Soppimath et al. ........... 514/394 |

FOREIGN PATENT DOCUMENTS

| DE | 159289 | 3/1983 |
| WO | WO-2010/036702 | 4/2010 |
| WO | WO-2010/148288 A2 | 12/2010 |
| WO | WO-2012/015810 A2 | 2/2012 |

OTHER PUBLICATIONS

PCT Notification of Transmittal of International Search Report and Written Opinion for PCT/US2013/032295.
PCT Written Opinion of International Search Authority for PCT/US2013/032295.
Search History: Limited Classification Search dated May 10, 2013, PCT/US2013/032295.
Biewenga, et al., "The Pharmacology of the Antioxidant Lipoic Acid," Gen. Pharmac., vol. 29, No. 3, pp. 315-331 (1997).
Rowe, et al., "Handbook of Pharmaceutical Excipients," 6th edition, pp. 454-455 (2009).
Spiegel, et al., "Use of Nonaqueous Solvents in Parenteral Products," J. Pharmac. Sciences, vol. 52, No. 10, pp. 917-927 (1963).
International Search Report PCT/US2011/022958 dated Apr. 12, 2011.
Maas B: "Stabilitaet von Bendamustinhydrochlorid in Infusionsloesungen" Die Pharmazie, Govi Verlag Pharmazeutischer Verlag GmbH, Eschborn, DE, vol. 49, No. 10, Jan. 1, 1994.

* cited by examiner

*Primary Examiner* — Renee Claytor
(74) *Attorney, Agent, or Firm* — Lucas & Mercanti, LLP

(57) ABSTRACT

Methods of treating bendamustine responsive conditions in patients having fluid and/or sodium intake restrictions are disclosed. The methods include identifying patients having such restrictions and in need of bendamustine, and then administering thereto a bendamustine-containing composition in a volume of about 120 ml or less intravenously over a period of about 15 minutes or less. The smaller volumes and reduced sodium load as compared to currently known methods of treatment minimize cardiac and/or renal stress in patients having diseases such as congestive heart failure or renal disease.

30 Claims, No Drawings

METHOD OF TREATING BENDAMUSTINE-RESPONSIVE CONDITIONS IN PATIENTS REQUIRING REDUCED VOLUMES FOR ADMINISTRATION

CROSS-REFERENCE TO RELATED APPLICATIONS

This application claims the benefit of priority from U.S. Provisional Patent Application Ser. No. 61/613,173, filed Mar. 20, 2012, 61/669,889, filed Jul. 10, 2012, and 61/678,715, filed Aug. 2, 2012, the disclosure of which is incorporated herein by reference.

BACKGROUND OF THE INVENTION

Bendamustine is used in the treatment of a number of cancers including leukemias, Hodgkin's disease and multiple myelomas. Bendamustine, (present as the HCl salt) is the active ingredient of the commercial product Treanda™, a lyophilized powder for reconstitution. Current labeling requirements call for the reconstituted product to be immediately (within 30 minutes) diluted into 500 mL of parenterally acceptable diluents such as 0.9% saline (normal saline) or 2.5% dextrose/0.45% saline and administered as part of an intravenous infusion delivering 100 mg/m$^2$ over 30 minutes or 120 mg/m$^2$ over 60 minutes. The diluted admixture may be stored at 2-8° C. for up to 24 hours, or 3 hours at room temperature (15-30° C.); administration must be completed within this period due to limited chemical stability in aqueous solutions.

Higher infusion volume and longer infusion times, however, are associated with many drawbacks. For example, currently available bendamustine therapies with their larger intravenous administration volumes and sodium loads can be contraindicated in patients who have significant cardiac disease such as congestive heart failure and/or renal failure. Thus, some patients who would benefit from bendamustine therapy cannot take the drug or, if there are no alternative therapies, are exposed to significant physical harm as a result of receiving large volumes of sodium-containing fluid along with the bendamustine. The higher infusion volumes cause unhealthy stress on diseased organs including the heart and kidney in these patients. It would be most advantageous if the drug could be administered in smaller volumes and over shorter times to patients needing the drug but also requiring fluid and sodium intake restrictions. The present invention addresses this need.

SUMMARY OF THE INVENTION

In a first aspect of the invention there are provided methods of treating a bendamustine-responsive condition in a subject requiring restricted fluid and/or sodium intake. The methods include
 a) identifying a subject in need of bendamustine therapy and having a physiological condition requiring restricted fluid and/or sodium intake;
 b) parenterally administering to the subject patient a volume of about 120 ml or less of a liquid composition containing:
  i) from about 0.05 to about 12.5 mg/ml of bendamustine or a pharmaceutically acceptable salt thereof;
  ii) a solubilizer comprising polyethylene glycol and propylene glycol, the polyethylene glycol being present in an amount of from about 0.3 to about to 45% volume and the propylene glycol being present in an amount of from about 0.03 to about 5% volume; and, optionally
  iii) a parenterally acceptable diluent,
over a substantially continuous period of less than or equal to about 30 minutes.

In alternative aspects of the invention, the methods are similar to that mentioned above, but the liquid compositions administered contain:

| Ingredient | Concentration Range (mg/ml) |
| --- | --- |
| Bendamustine HCl | 0.05 to 1.6 |
| Solubilizer 1 propylene glycol | 0.3 to 6.5 |
| Solubilizer 2 PEG 400 | 3.3 to 65 |
| Monothioglycerol | 0.02 to 0.35 |
| NaOH | 0.0 to 0.01 |

| Ingredient | Concentration Range (mg/ml) |
| --- | --- |
| Bendamustine HCl | 1.1 to 12.5 |
| Solubilizer 1 propylene glycol | 4.5 to 51 |
| Solubilizer 2 PEG 400 | 45 to 500 |
| Monothioglycerol | 0.2 to 2.5 |
| NaOH | 0.0 to 0.04. |

As was the case with the first aspect, the compositions administered can optionally include a parenterally acceptable diluent such as 0.9% NaCl, i.e. normal saline, or 0.45% NaCl. The time period during which the formulation is administered is preferably less than or equal to about 30 minutes but can be as brief as about 5 minutes or less, for example, when bolus doses of smaller volumes are administered.

The methods of the present invention take advantage of the fact that the concentration of the bendamustine HCl is below the room temperature solubility limit of the vehicle into which it is placed. As a result, the bendamustine does not precipitate during administration to the patient. This is advantageous because the enhanced solubility of the drug allows it to be administered in much smaller volumes than the standard 500 ml administration volume. Patients with medical conditions benefiting from reduced sodium and/or fluid intake can have bendamustine therapy without the NaCl load associated with a typical 500 ml normal saline diluent. In fact, the methods of the present invention allow the diluent volume to be reduced by at least 80% (100 ml vs. 500 ml) or more in view volumes being as low as about 15 ml or less. Commensurate reductions in sodium necessarily occur by virtue of the smaller volumes administered.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

In accordance with a first aspect of the invention there are provided methods of treating conditions responsive to bendamustine treatment in patients, preferably humans, requiring such treatment and further requiring or benefiting from restricted fluid and/or sodium intake. Without limiting the scope of the invention, treatments which are known to be responsive to bendamustine therapy include cancer or malignant disease generally and more specifically, chronic lymphocytic leukemia (CLL), indolent B-cell non-Hodgkin's lymphoma, Hodgkin's disease, multiple myelomas as well as other conditions know to those of ordinary skill as being responsive to bendamustine therapy. For purposes of the present invention, the step of selecting of patients or subjects suitable for inclusion in the inventive methods shall be understood to be one of medical or clinical assessment which involves determination of the physical unsuitability of receiving excessive fluid volumes and/or sodium due to congestive heart failure, renal impairment or other clinical indicia readily apparent to those of ordinary skill.

The methods include a) identifying and/or selecting a subject, e.g. a human patient, who is in need of both bendamustine therapy and who has or who would benefit from one or more of fluid and/or sodium intake restrictions; and b) parenterally administering to the subject, preferably by the intravenous route and as a single dose, a volume of about 120 ml or less of a liquid bendamustine-containing composition which contains:

i) from about 0.05 to about 12.5 mg/ml of bendamustine or a pharmaceutically acceptable salt thereof;

ii) a solubilizer comprising polyethylene glycol and propylene glycol, the polyethylene glycol being present in an amount of from about 0.3 to about to 45% volume and the propylene glycol being present in an amount of from about 0.03 to about 5% volume; and, optionally iii) a parenterally acceptable diluent, over a substantially continuous period of less than or equal to about 30 minutes.

The solubilizer portion of the formulation preferably includes from about 0.3 to about 45% volume polyethylene glycol (PEG) and from about 0.03 to about 5% volume propylene glycol (PG), as calculated on the basis of the total or final volume administered. Stated alternatively, the final concentration of the PEG generally ranges from about 3 to about 500 mg/ml, while the final concentration of the PG generally ranges from about 0.5 to about 51 mg/ml. Within these general ranges, certain aspects of the invention include concentration ranges for the PEG of from about 45 to about 500 mg/ml or from about 3.3 to about 63.3 mg/ml. The PG will range of from about 4.7 to about 50.6 mg/ml; or from about 0.02 to about 6.5 mg/ml.

The solubilizer is preferably a mixture of polyethylene glycol, hereinafter "PEG" and propylene glycol, hereinafter "PG". The solubilizer can also optionally include an antioxidant such as monothioglycerol. The amount of antioxidant included is a formulation stabilizing amount, which, in the case of monothioglycerol ranges from about 2 to about 10 mg/ml. The PEG preferably has a molecular weight of about 400, i.e. PEG 400. Other molecular weight PEG's known to those of ordinary skill can be included if desired in alternative embodiments.

Certain aspects of the invention call for the ratio of the PEG to PG found in the solubilizer to be about 90:10. In alternative aspects, the ratio of the PEG to PG is about 85:15.

In some aspects of the invention, the total amount of solubilizer, i.e. blend of PEG and PG, included in infusion volumes of about 100-115 ml is from about 0.5 to about 26.5% vol.; while solubilizer amounts of from about 2.0 to about 22.4% vol. included in infusion volumes of about 50-65 ml.

Since the solubilizer is a blend, the amount of PEG and PG in various volumes (calculated as % vol.) can be as follows:

| Solubilizer | 50 ml | 100 ml |
|---|---|---|
| PEG | 20.12 | 11.33 |
| PG | 2.24 | 1.26. |

In some aspects of the invention, the bendamustine is administered intravenously as part of an intravenous infusion. Contemplated infusion volumes are preferably less than 120 ml with volumes such as about 100 ml, 50 ml, 30 ml, 15 ml or less, with each volume varying about +/−10% or +/−15% being preferred in some embodiments. In alternative aspects of the invention, the intravenous administration volume is suitable for IV bolus administration and may also include an amount of pharmaceutically acceptable diluent such as normal saline or one of the other diluents described herein which does not cause the solubility of the vehicle to fall below the concentration of the bendamustine. Stated alternatively, the final concentration of the bendamustine will be below the solubility of the combination vehicle containing the mixture of propylene glycol and PEG and diluent. As such, smaller volumes are required to deliver therapeutic doses to patients and the patients are spared exposure to excess fluid and sodium during therapy.

While most aspects of the invention are described in the context of administering less than about 120 ml including all vehicle ingredients, excipients, etc., it should be appreciated that volumes as low as a few milliliters, e.g. about 2, can be used so long as the vehicle includes sufficient solubilizers to preserve the solubility of the bendamustine therein during administration to the patient.

For purposes of the present invention, the word "about" when used to modify infusion volumes or concentrations shall be understood to include values which may vary by amounts of about +/−10% or 15%.

In certain embodiments where the infusion volume is about 50 ml, the concentration of the bendamustine HCl or other pharmaceutically acceptable salt thereof is preferably from about 0.5 to about 5.6 mg/ml. In embodiments where the infusion volume is about 100 ml, the concentration of the bendamustine HCl or other pharmaceutically acceptable salt thereof can be preferably from about 0.1 to about 3.2 mg/ml.

The bendamustine compositions are preferably infused intravenously over a time period of about 10 minutes or less when the volume is about 50 ml; and over a time period of about 15 minutes or less when the intravenous infusion volume is about 100 ml. Shorter time periods are contemplated for volumes below 50 ml, i.e. 2, 5, 10 or 15 to 30 ml where IV bolus or IV push administration is used.

The infusible compositions in many aspects of the invention will also preferably include the parenterally acceptable diluents such as 0.9% saline (normal saline, preferred), 0.45% saline (half normal saline, also preferred) or 2.5% dextrose/0.45% saline. Alternative diluents such as water for injection (WFI) are also contemplated.

Formulations well suited for carrying out the methods described herein are also described in commonly assigned U.S. patent application Ser. No. 13/016,473, filed Jan. 28, 2011, and U.S. Ser. No. 13/767,672 filed Feb. 14, 2013, the contents of which are incorporated herein by reference. As reviewed in the '672 patent application, some preferred bendamustine formulations can also include a minor amount of a pH adjuster such as sodium formate, sodium phosphate, potassium hydroxide, phosphoric acid or, preferably, sodium hydroxide. Preferably, the amount of sodium included as part of the once daily administration is less than or equal to about 8-16 meq's of sodium per 100 ml administration and less than or equal to about 4-8 meq's of sodium per 50 ml administration. The treatments of the present invention therefore provide a significant reduction in sodium intake as compared to currently available treatments which deliver 40-80 meq's of sodium as part of every larger volume infusion needed to deliver the same amount of bendamustine.

In an alternative embodiment of the invention, the bendamustine formulations used in the methods described herein can be one or more of those described in U.S. Pat. Nos. 8,344,006 and 8,076,366; and US Patent Application Nos. 2013/0041004; 2012/0071532; 2010/0216858; 2006/0159713; and 2013/0041003, the contents of each of which are incorporated herein by reference. It being understood that the vehicle into which the bendamustine HCl is placed will have sufficient bendamustine solubility which exceeds the concentration of the drug included therein.

If desired, a sufficient amount of a concentrated, ready to use liquid formulation such one containing 25 mg/ml bendamustine HCl and already admixed with sufficient solubilizers can be transferred to a suitable fixed volume diluent container such as a bag containing 50 or 100 ml normal saline or the like. Alternatively, lyophilized bendamustine HCl can be reconstituted, combined with sufficient solubilizer blends as described herein and administered in accordance with the inventive methods. In such embodiments, the actual amount delivered to the patient will be slightly more than the diluent amount so as to allow for the addition of the drug/solubilizer vehicle.

Without limitation, patients in need of both bendamustine therapy and restricted fluid and/or sodium intake include: a) patients suffering from congestive heart failure (CHF) disease; the disease can be of the mild, moderate to severe type CHF; b) patients suffering from any number of renal diseases in which fluid restrictions are mandated or desirable, including temporary (acute) or chronic renal suppression or renal insufficiency, acute or chronic kidney failure, etc.

Those aspects of the invention related to treatment of patients having renal disease or a predisposition toward renal suppression with lower infusion volumes have significant therapeutic benefits as compared to currently approved treatments requiring larger infusion volumes. For example, elderly lymphoma patients are predisposed to renal difficulties due to their age and disease. They are often likely to develop renal difficulties subsequent to treatment initiation if the condition is not present prior to the start of therapy. Acute renal failure is an adverse effect already recognized as being associated with current treatments, often occurring during the first or second cycles. Many of those patients who do not present with acute renal failure nonetheless suffer from some form of renal suppression. Consequently, delivering bendamustine in accordance with the methods of the present invention will significantly lessen the incidence of renal injury in patients requiring treatment for a bendamustine-treatable condition. The methods described herein thus offer an alternative when standard volume, i.e. 500 ml, infusions of bendamustine is contraindicated.

In some preferred aspects of the invention, methods of treating or preventing chronic lymphocytic leukemia (CLL) in a patient having fluid and/or sodium intake restrictions are provided. The patient requiring such treatment is identified and administered within a time period of about 30 minutes or less, a therapeutic amount of bendamustine in a volume of 120 ml or less and a sufficient amount of a solubilizer mixture as described herein e.g. from about 0.2 to 27% vol. of a solubilizer comprising polyethylene glycol and propylene glycol; and, if desirable, a parenterally acceptable diluent.

The small volume infusions described herein, e.g. 50 or 100 ml solutions containing therapeutically effective amounts of bendamustine HCl, can be given as part of any CLL treatment protocol in which bendamustine is included. Thus, the compositions described herein can be administered as part of a poly-pharmaceutical treatment regimen according to known protocols with the exception that the concentrated bendamustine compositions described herein are administered in smaller infusion volumes over significantly shorter administration periods than those currently used. For example, some CLL treatment regimens can include administering the compositions described herein intravenously as part of about 100 ml infusions in about 15 minutes or less on days 1 and 2 of a 28 day cycle and repeating the cycle up to 6 times, or longer if clinically appropriate. If 50 ml volumes are used to deliver the bendamustine, the time of administration is preferably about 10 minutes or less. In spite of the smaller volumes, the amount of bendamustine HCl administered to the patient in need thereof per dose (infusion) in some preferred embodiments is about 100 mg/m$^2$. In some alternative aspects of the invention, the amount of bendamustine HCl administered to the patient in need thereof as part of the 50 or 100 ml infusion is an amount sufficient to provide a dosage of 50 or 25 mg/m$^2$. Additional administration dosages will be apparent to those of ordinary skill based upon clinical experience, patient need without undue experimentation.

In another aspect of the invention, methods of treating or preventing the malignant disease of indolent B-cell non-Hodgkin's lymphoma in a patient having fluid and/or sodium intake restrictions are provided. Similar to the above-mentioned therapy, a patient requiring such treatment is identified and a small volume bendamustine-containing composition is administered thereto over a period of 15 minutes or less.

More specifically, the bendamustine-containing composition can be administered intravenously as a 100 ml infusion in about 15 minutes or less on days 1 and 2 of a 21 day cycle for up to 8 cycles, or longer if clinically appropriate. If 50 ml volumes are used to deliver the bendamustine, the time of administration is preferably about 10 minutes or less. The amount of bendamustine administered to the subject is preferably about 120 mg/m$^2$, although in alternative embodiments, the amount administered can be about 90 or 60 mg/m$^2$.

It will be appreciated by those skilled in the art that the above-mentioned dosages calculated in mg/m$^2$ for purposes of body surface area (BSA) are consistent with the bendamustine HCl concentrations also described herein, e.g. 0.5 to 5.6 mg/ml.

In an alternative aspect of the invention, the methods treating a bendamustine-responsive condition in subjects requiring restricted fluid and/or sodium intake include a) identifying a subject in need of bendamustine therapy and having a physiological condition requiring restricted fluid and/or sodium intake;

b) parenterally administering to said subject a volume of about 120 ml or less of a liquid composition containing:

| Ingredient | Concentration Range (mg/ml) |
|---|---|
| Bendamustine HCl | 0.05 to 1.6 |
| Solubilizer 1 propylene glycol | 0.3 to 6.5 |
| Solubilizer 2 PEG 400 | 3.3 to 65 |
| Monothioglycerol | 0.02 to 0.35 |
| NaOH | 0.0 to 0.01 | and, optionally a parenterally acceptable diluent, over a substantially continuous period of less than or equal to about 30 minutes. More preferably, the administration time is well below 30 minutes and the administration time will decrease as the volume administered decreases.

Bendamustine formulations containing the above ingredients are capable of delivering approximately 25 mg of the drug as the HCl salt in volumes of pharmaceutically acceptable diluent ranging from about 120 ml down to about 15 ml. For example, 1 ml of a bendamustine HCl ready to use liquid available from Eagle Pharmaceuticals containing

| Ingredient | Concentration (mg/ml) |
|---|---|
| Bendamustine HCl | 25 |
| PG | 103.2 |
| PEG 400 | 1013.4 |
| Monothioglycerol | 5 |
| NaOH | 0.08 | is combined with 100 ml of a normal saline diluent to provide a final IV infusion containing 101 ml and a bendamustine final concentration of 0.25 mg/ml.

One ml of the 25 mg/ml Eagle bendamustine HCl is diluted into additional diluent volumes as shown below:

| Diluent Volume (ml) | Final Volume (ml) | Final Bendamustine Conc. (mg/ml) |
|---|---|---|
| 50 | 51 | 0.49 |
| 30 | 31 | 0.81 |
| 15 | 16 | 1.56. |

The measured solubility of the bendamustine HCl in the diluent/solubilizer combination (50 ml diluent+1 ml of 25 mg/ml bendamustine HCl and solubilizers, etc.) at room temperature was 10.5 mg/ml using normal saline and 14.2 mg/ml using half normal saline/dextrose. The solubility of the diluent/solubilizer combination far exceeded the bendamustine concentration, thus assuring the avoidance of precipitated drug prior to or during administration. As will be appreciated by those of ordinary skill, as the concentration of solubilizers increases with respect to the total volume in small administration doses, the solubility of the bendamustine is maintained.

In a related embodiment of this aspect of the invention, the methods include treating a bendamustine-responsive condition in a subject requiring restricted fluid and/or sodium intake, by
a) identifying a subject in need of bendamustine therapy and having a physiological condition requiring restricted fluid and/or sodium intake;
b) parenterally administering to said subject a volume of about 120 ml or less of a liquid composition containing:

| Ingredient | Concentration Range (mg/ml) |
|---|---|
| Bendamustine HCl | 1.1 to 12.5 |
| Solubilizer 1 propylene glycol | 4.5 to 51 |
| Solubilizer 2 PEG 400 | 45 to 500 |
| Monothioglycerol | 0.2 to 2.5 |
| NaOH | 0.0 to 0.04 | and, optionally a parenterally acceptable diluent, over a substantially continuous period of less than or equal to about 30 minutes. As was the case above, the administration time will decrease with the decrease in volume administered.

Bendamustine formulations containing the above ingredients are capable of delivering approximately 360 mg of the drug as the HCl salt in volumes of pharmaceutically acceptable diluent ranging from about 120 ml down to about 15 ml. As was the case above, the measured solubility of the bendamustine HCl in the diluent/solubilizer combination (1 ml drug+solubilizers, etc. and 50 ml diluent) at room temperature was 10.5 mg/ml using normal saline and 14.2 mg/ml using half normal saline/dextrose.

Instead of using only 1 ml of the above described Eagle 25 mg/ml bendamustine HCl ready to use liquid, 14.4 ml is combined with various amounts of diluent.

| Diluent Volume (ml) | Final Volume (ml) | Final Bendamustine Conc. (mg/ml) |
|---|---|---|
| 100 | 114.4 | 3.15 |
| 50 | 64.4 | 5.59 |
| 30 | 44.4 | 8.11 |
| 15 | 29.4 | 12.24 |

In each case, the solubility of the diluent/solubilizer combination exceeds the bendamustine concentration, thus assuring the avoidance of precipitated drug prior to or during administration.

EXAMPLES

The following examples serve to provide further appreciation of the invention but are not meant in any way to restrict the effective scope of the invention.

Example 1

In this example, a patient diagnosed with chronic lymphocytic leukemia (CLL) and having chronic kidney disease (GFR<30 ml/min/1.73 m$^2$) is begun on a treatment protocol with bendamustine. In particular, the patient is administered 360 mg of bendamustine as part of an approximately 114.4 ml infusion on days 1 and 2 of a 28 day cycle. The intravenous formulation is prepared by drawing up 14.4 ml of an RTU (ready to use) liquid containing bendamustine HCl 25 mg/ml, PG 103.2 mg/ml, PEG 1013.4 mg/ml, monothioglycerol 5 mg/ml and 0.08 mg/ml NaOH and mixing it into a 100 ml bag containing 0.9% NaCl. The final bendamustine concentration for the IV fluid is 3.15 mg/ml. The infusion is administered to the patient in less than 15 minutes. No precipitated bendamustine is observed in the IV fluid during administration.

Example 2

The process of Example 1 is repeated except that the IV infusion volume is approximately 64.4 ml. The same 14.4 ml of an RTU (ready to use) liquid containing bendamustine HCl 25 mg/ml, PG 103.2 mg/ml, PEG 1013.4 mg/ml, monothioglycerol 5 mg/ml and 0.08 mg/ml NaOH is used and it is mixed into a 50 ml bag containing 0.9% NaCl. The final bendamustine concentration for the IV fluid is 5.59 mg/ml. The infusion is administered to the patient in less than 10 minutes. No precipitated bendamustine is observed in the IV fluid during administration.

Example 3

In this Example, the process of Example 1 is repeated except that lyophilized bendamustine HCl is reconstituted with a solubilizer mixture containing PEG:PG (90:10) before dilution into the 100 ml bag containing normal saline.

We claim:

1. A method of treating a bendamustine-responsive condition in a subject requiring restricted fluid and/or sodium intake, comprising
   a) identifying a subject in need of bendamustine therapy and having a physiological condition requiring restricted fluid and/or sodium intake;
   b) parenterally administering to said subject a volume of about 100 ml or less of a liquid composition containing:
      i) from about 0.05 to about 12.5 mg/ml of bendamustine or a pharmaceutically acceptable salt thereof;
      ii) a solubilizer comprising polyethylene glycol and propylene glycol, the polyethylene glycol being present in an amount of from about 0.3 to about to 45% volume and the propylene glycol being present in an amount of from about 0.03 to about 5% volume; and, optionally
      iii) a parenterally acceptable diluent
   over a substantially continuous period of less than or equal to about 30 minutes.

2. The method of claim 1, wherein the diluent comprises 0.9% NaCl or 0.45% NaCl.

3. The method of claim 1, wherein the subject has congestive heart disease.

4. The method of claim 1, wherein the subject has renal insufficiency.

5. The method of claim 4, wherein the renal insufficiency is renal failure or renal suppression.

6. The method of claim 1, wherein the concentration of the bendamustine or pharmaceutically acceptable salt is from about 0.1 to about 3.2 mg/ml.

7. The method of claim 1, wherein the concentration of the bendamustine or pharmaceutically acceptable salt is from about 0.5 to about 5.6 mg/ml.

8. The method of claim 1, wherein the amount of solubilizer is from about 0.5 to about 26.5% vol.

9. The method of claim 1, wherein the amount of solubilizer is from about 2.0 to about 22.4% vol.

10. The method of claim 1, where the polyethylene glycol is PEG 400.

11. The method of claim 1, wherein the weight ratio of polyethylene glycol to propylene glycol is about 90:10.

12. The method of claim 1, wherein the weight ratio of polyethylene glycol to propylene glycol is about 85:15.

13. The method of claim 1, wherein the volume administered is about 50, 30 or 15 ml.

14. The method of claim 1, wherein the composition further comprises monothioglycerol and NaOH.

15. The method of claim 7, wherein the volume administered is about 50 ml+/−15% or less and the composition is administered over a time period of about 10 minutes or less.

16. The method of claim 6, wherein the volume administered is about 100 ml+/−15% or less and the composition is administered over a time period of about 15 minutes or less.

17. The method of claim 1, wherein the parenterally acceptable diluent is 0.9% NaCl (normal saline).

18. The method of claim 1, wherein the bendamustine-responsive condition is chronic lymphocytic leukemia.

19. The method of claim 18, wherein the composition is administered intravenously in a volume of about 50 ml over a time period of about 10 minutes or less on days 1 and 2 of a 28 day cycle.

20. The method of claim 18, wherein the composition is administered intravenously in a volume of about 100 ml over a time period of about 15 minutes or less on days 1 and 2 of a 28 day cycle.

21. The method of claim 18, wherein the composition is administered for up to 6 cycles.

22. The method of claim 18, wherein the volume of the composition administered to the subject provides a dosage amount ranging from about 25 mg/m$^2$ to about 100 mg/m$^2$ to the subject.

23. The method of claim 1, wherein the bendamustine-responsive condition is indolent B-cell non-Hodgkin's lymphoma.

24. The method of claim 23, wherein the composition is administered intravenously in a volume of about 50 ml over a time period of about 10 minutes or less on days 1 and 2 of a 21 day cycle.

25. The method of claim 23, wherein the composition is administered intravenously in a volume of about 100 ml over a time period of about 15 minutes or less on days 1 and 2 of a 21 day cycle.

26. The method of claim 23, wherein the composition is administered for up to 8 cycles.

27. The method of claim 23, wherein the volume of the composition administered to the subject provides a dosage amount ranging from about 60 mg/m$^2$ to about 120 mg/m$^2$ to the subject.

28. A method of treating a bendamustine-responsive condition in a subject requiring restricted fluid and/or sodium intake, comprising
   a) identifying a subject in need of bendamustine therapy and having a physiological condition requiring restricted fluid and/or sodium intake;
   b) parenterally administering to said subject a volume of about 100 ml or less of a liquid composition containing:

| Ingredient | Concentration Range (mg/ml) |
| --- | --- |
| Bendamustine HCl | 0.05 to 1.6 |
| Solubilizer 1 propylene glycol | 0.3 to 6.5 |
| Solubilizer 2 PEG 400 | 3.3 to 65 |
| Monothioglycerol | 0.02 to 0.35 |
| NaOH | 0.0 to 0.01 | and, optionally a parenterally acceptable diluent, over a substantially continuous period of less than or equal to about 30 minutes.

29. A method of treating a bendamustine-responsive condition in a subject requiring restricted fluid and/or sodium intake, comprising
   a) identifying a subject in need of bendamustine therapy and having a physiological condition requiring restricted fluid and/or sodium intake;
   b) parenterally administering to said subject a volume of about 100 ml or less of a liquid composition containing:

| Ingredient | Concentration Range (mg/ml) |
| --- | --- |
| Bendamustine HCl | 1.1 to 12.5 |
| Solubilizer 1 propylene glycol | 4.5 to 51 |
| Solubilizer 2 PEG 400 | 45 to 500 |
| Monothioglycerol | 0.2 to 2.5 |
| NaOH | 0.0 to 0.04 | and, optionally a parenterally acceptable diluent, over a substantially continuous period of less than or equal to about 30 minutes.

30. A method according to claim 1, wherein the bendamustine is present as the hydrochloride salt.

* * * * *